(12) United States Patent
Jin

(10) Patent No.: US 9,269,910 B2
(45) Date of Patent: Feb. 23, 2016

(54) SUBSTITUTED CARBAZOLES AS HOLE TRANSPORT MATERIALS FOR ORGANIC ELECTROLUMINESCENCE DEVICES AND ORGANIC ELECTROLUMINESCENCE DEVICES COMPRISING THE SAME

(71) Applicant: SAMSUNG DISPLAY CO., LTD., Yongin, Gyeonggi-Do (KR)

(72) Inventor: Xiulan Jin, Yongin (KR)

(73) Assignee: SAMSUNG DISPLAY CO., LTD., Yongin, Gyeonggi-Do (KR)

( * ) Notice: Subject to any disclaimer, the term of this patent is extended or adjusted under 35 U.S.C. 154(b) by 0 days.

(21) Appl. No.: 14/091,472

(22) Filed: Nov. 27, 2013

(65) Prior Publication Data

US 2014/0155601 A1 Jun. 5, 2014

(30) Foreign Application Priority Data

Nov. 30, 2012 (JP) .................. 2012-263843

(51) Int. Cl.

| *C07D 209/86* | (2006.01) |
|---|---|
| *H01L 51/00* | (2006.01) |
| *C07D 405/14* | (2006.01) |
| *C07D 409/12* | (2006.01) |
| *C07D 409/14* | (2006.01) |
| *H01L 51/50* | (2006.01) |

(52) U.S. Cl.
CPC .......... *H01L 51/0072* (2013.01); *C07D 405/14* (2013.01); *C07D 409/12* (2013.01); *C07D 409/14* (2013.01); *H01L 51/0061* (2013.01); *H01L 51/0065* (2013.01); *H01L 51/0067* (2013.01); *H01L 51/0074* (2013.01); *H01L 51/5056* (2013.01)

(58) Field of Classification Search
CPC .................................... C07D 209/86
USPC ............... 544/180, 333; 546/268.1; 548/440; 549/43, 460
See application file for complete search history.

(56) References Cited

FOREIGN PATENT DOCUMENTS

| JP | 2010-241801 A | 10/2010 |
|---|---|---|
| JP | 2010-254674 A | 11/2010 |
| KR | 10-2008-0092890 A | 10/2008 |
| KR | 10-2012-0009761 A | 2/2012 |
| KR | 10-2012-0013173 A | 2/2012 |
| WO | WO-2010-061824 A1 | 6/2010 |
| WO | WO-2010-110553 A2 | 9/2010 |
| WO | WO-2010-114017 A1 | 10/2010 |
| WO | WO-2011-133007 A2 | 10/2011 |
| WO | WO-2012-000756 A1 | 1/2012 |

*Primary Examiner* — Douglas M Willis
(74) *Attorney, Agent, or Firm* — Lee & Morse, P.C.

(57) ABSTRACT

A hole transport material for an organic electroluminescence (EL) device, and an EL device including the same, the hole transport material being represented by Formula 1, below:

[Formula 1]

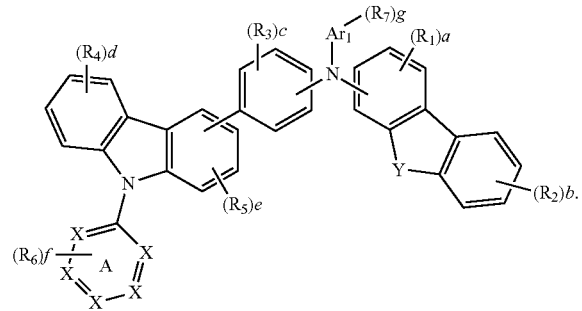

2 Claims, 1 Drawing Sheet

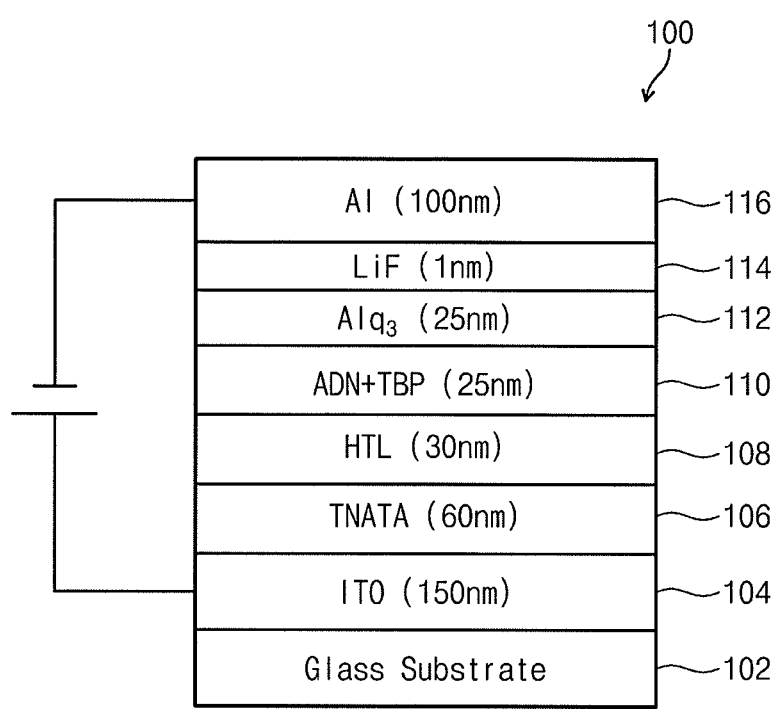

SUBSTITUTED CARBAZOLES AS HOLE TRANSPORT MATERIALS FOR ORGANIC ELECTROLUMINESCENCE DEVICES AND ORGANIC ELECTROLUMINESCENCE DEVICES COMPRISING THE SAME

CROSS-REFERENCE TO RELATED APPLICATION

Japanese Patent Application No. 2012-263843, filed on Nov. 30, 2012, in the Japanese Patent Office, and entitled: "HOLE TRANSPORT MATERIAL FOR ORGANIC ELECTROLUMINESCENCE DEVICE AND ORGANIC ELECTROLUMINESCENCE DEVICE USING THE SAME," is incorporated by reference herein in its entirety.

BACKGROUND

1. Field

Embodiments relate to a hole transport material for an organic electroluminescence device, and an organic electroluminescence device including the same.

2. Description of the Related Art

In recent years, organic electroluminescence (EL) displays are one type of image displays that have been actively developed. Unlike a liquid crystal display (or the like), the organic EL display is so-called a self-luminescent display that recombines holes and electrons injected from an anode and a cathode in a light-emitting layer to thus emit light from a light-emitting material including an organic compound, thereby displaying an image.

An example of a light-emitting device (hereinafter referred to as an organic EL device) may include an organic EL device (that includes an anode, a hole transport layer on the anode, a light-emitting layer on the hole transport layer, an electron transport layer on the light-emitting layer, and a cathode on the electron transport layer). Holes injected from the anode may be injected into the light-emitting layer via the hole transport layer. Electrons may be injected from the cathode, and then injected into the light-emitting layer via the electron transport layer. The holes and the electrons injected into the light-emitting layer may be recombined to generate excitons within the light-emitting layer. The organic EL device may emit light generated by radiation and non-activation of the excitons.

SUMMARY

Embodiments are directed to a hole transport material for an organic electroluminescence device, and an organic electroluminescence device including the same.

The embodiments may be realized by providing a hole transport material for an organic electroluminescence (EL) device, the hole transport material being represented by Formula 1, below:

[Formula 1]

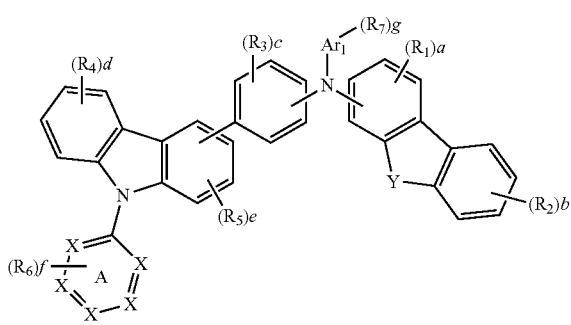

wherein $Ar_1$ is an aryl group having 6 to 20 carbon atoms, $R_1$ to $R_7$ are each independently a substituted or unsubstituted straight-chain alkyl group having 1 to 10 carbon atoms, a substituted or unsubstituted branched-chain alkyl group having 3 to 10 carbon atoms, a substituted or unsubstituted aryl group having 6 to 20 carbon atoms, or a heteroaryl group having 5 to 20 carbon atoms, a to g are integers indicating the number of substituent $R_1$ to $R_7$, each $R_1$ is different from or the same as each other $R_1$, each $R_2$ is different from or the same as each other $R_2$, each $R_3$ is different from or the same as each other $R_3$, each $R_4$ is different from or the same as each other $R_4$, each $R_5$ is different from or the same as each other $R_5$, each $R_6$ is different from or the same as each other $R_6$, each $R_7$ is different from or the same as each other $R_7$, X of ring A is a methine group, a carbon atom, or a nitrogen atom, and Y is an oxygen atom or a sulfur atom.

1 to 3 of the Xs may be nitrogen atoms.

At least one of the Xs of ring A may be the carbon atom.

a to g may satisfy the following relations: $0 \leq a \leq 3$, $0 \leq b \leq 4$, $0 \leq c \leq 4$, $0 \leq d \leq 4$, $0 \leq e \leq 3$, $0 \leq f \leq 4$, and $0 \leq g \leq 5$.

The embodiments may also be realized by providing an organic EL device including a hole transport layer formed of a hole transport material represented by Formula 1, below:

[Formula 1]

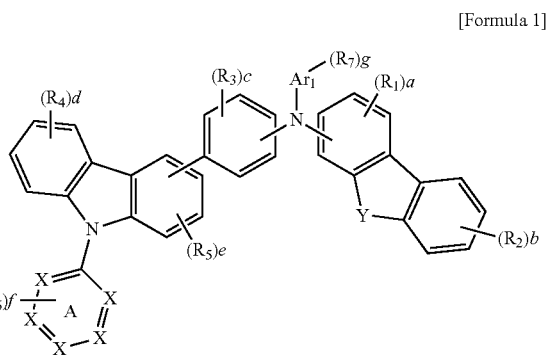

wherein $Ar_1$ is an aryl group having 6 to 20 carbon atoms, $R_1$ to $R_7$ are each independently a substituted or unsubstituted straight-chain alkyl group having 1 to 10 carbon atoms, a substituted or unsubstituted branched-chain alkyl group having 3 to 10 carbon atoms, a substituted or unsubstituted aryl group having 6 to 20 carbon atoms, or a heteroaryl group having 5 to 20 carbon atoms, a to g are integers indicating the number of substituent $R_1$ to $R_7$, each $R_1$ is different from or the same as each other $R_1$, each $R_2$ is different from or the same as each other $R_2$, each $R_3$ is different from or the same as each other $R_3$, each $R_4$ is different from or the same as each other $R_4$, each $R_5$ is different from or the same as each other $R_5$, each $R_6$ is different from or the same as each other $R_6$, each $R_7$ is different from or the same as each other $R_7$, X of ring A is a methine group, a carbon atom, or a nitrogen atom, and Y is an oxygen atom or a sulfur atom.

1 to 3 of the Xs may be nitrogen atoms.

At least one of the Xs of ring A may be the carbon atom.

a to g may satisfy the following relations: $0 \leq a \leq 3$, $0 \leq b \leq 4$, $0 \leq c \leq 4$, $0 \leq d \leq 4$, $0 \leq e \leq 3$, $0 \leq f \leq 4$, and $0 \leq g \leq 5$.

BRIEF DESCRIPTION OF THE DRAWING

Features will be apparent to those of skill in the art by describing in detail exemplary embodiments with reference to the attached drawing in which:

FIG. 1 illustrates a schematic cross-sectional view of an organic EL device according to an embodiment.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing FIGURE, the dimensions of layers and regions may be exaggerated for clarity of illustration. Like reference numerals refer to like elements throughout.

The embodiments provide a high efficiency and long life span organic EL device by using a hole transport material for an organic EL device. For example, an azaaryl substituent may be introduced as a hetero ring at a position of a nitrogen atom in a carbazole group, and a hetero ring (e.g., dibenzofuran or the like) may be introduced as a substituent of a triarylamine group.

A hole transport material for an organic EL device according to an embodiment may be an amine derivative compound represented by Formula 1, below. For example, the compound may include a carbazole group substituted with an azaaryl substituent and may include a hetero ring at a position of or bound to a triarylamine.

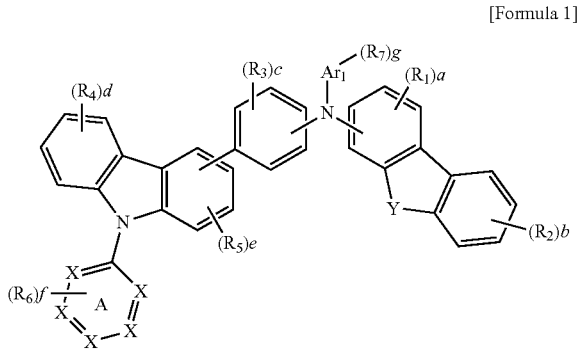

[Formula 1]

In Formula 1, $Ar_1$ may be an aryl group having 6 to 20 carbon atoms. $R_1$ to $R_7$ may each independently be a substituted or unsubstituted straight-chain alkyl group having 1 to 10 carbon atoms, a substituted or unsubstituted branched-chain alkyl group having 1 to 10 carbon atoms, a substituted or unsubstituted aryl group having 6 to 20 carbon atoms, or a heteroaryl group having 5 to 20 carbon atoms. a to g may be integers indicating a number of substituent $R_1$ to $R_7$. In an implementation, each $R_1$ may be different from or the same as each other $R_1$, each $R_2$ may be different from or the same as each other $R_2$, each $R_3$ may be different from or the same as each other $R_3$, each $R_4$ may be different from or the same as each other $R_4$, each $R_5$ may be different from or the same as each other $R_5$, each $R_6$ may be different from or the same as each other $R_6$, each $R_7$ may be different from or the same as each other $R_7$. X of ring A may be a methine group, a carbon atom, or a nitrogen atom. Y may be an oxygen or sulfur atom. In an implementation, in ring A, adjacent Xs may not both be nitrogen atoms.

The hole transport material may include a N-(azaaryl)carbazole group in which an azaaryl substituent is introduced as a hetero ring on a nitrogen atom in carbazole. In an implementation, in ring A, 1 to 3 of the five Xs may be nitrogen atoms. Maintaining the number of nitrogen atoms at 1 to 3 may help prevent a reduction in structural stability. Also, in ring A, at least one of the Xs may be a carbon atom. If a bond between adjacent nitrogen atoms were to be formed in ring A, the structural stability may be reduced. Accordingly, as noted above, in an implementation, in ring A, adjacent Xs may not both be nitrogen atoms. The hole transport material for an organic EL device may have the above-described structural characteristics. Thus, the electron affinity may be improved, and driving the organic EL device at a low voltage may be facilitated. Also, a nitrogen hetero ring may be included at a position on the carbazole. Thus, the hole transport material may not be used for a light-emitting layer, may help improve resistance to electrons arriving at the hole transport layer, and may realize long life span.

The hole transport material for an organic EL device according to an embodiment may include, e.g., dibenzofuran or dibenzothiophene, as a hetero ring (e.g., of fluorene) substituted on a tertiary amine. Thus, the hole transport material may help improve the organic EL device and realize long life span.

In an implementation, the hole transport material for an organic EL device according to an embodiment may be represented by Formula 1, above, where $Ar_1$ is an aryl group having 6 to 20 carbon atoms, $R_1$ to $R_7$ are each independently a substituted or unsubstituted straight-chain alkyl group having 1 to 10 carbon atoms, a substituted or unsubstituted branched-chain alkyl group having 1 to 10 carbon atoms, a substituted or unsubstituted aryl group having 6 to 20 carbon atoms or group having 6 to 20 carbon atoms heteroaryl group having 6 to 20 carbon atoms. Also, a to g may satisfy the following relations: 0≤a≤3, 0≤b≤4, 0≤c≤4, 0≤d≤4, 0≤e≤3, 0≤f≤4, and 0≤g≤5. In an implementation, the hole transport material may be substituted with a functional group, and the hole transport material may form a high efficiency and long life span hole transport layer.

In an implementation, the hole transport material for an organic EL device according to an embodiment may include, e.g., one of compounds 4 to 10, below.

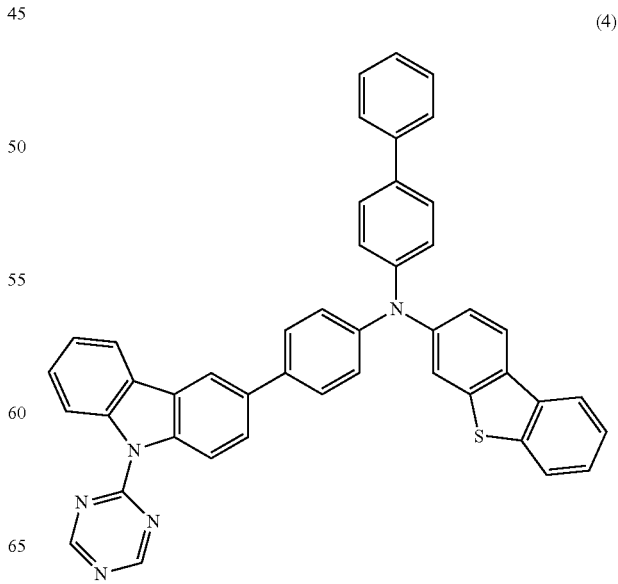

(4)

(5)
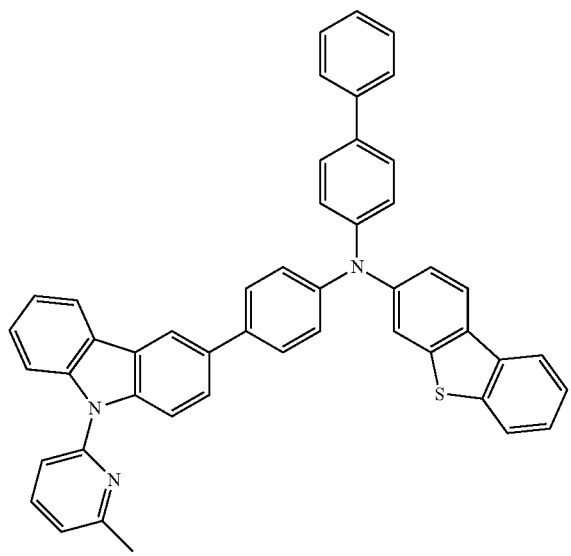
(6)
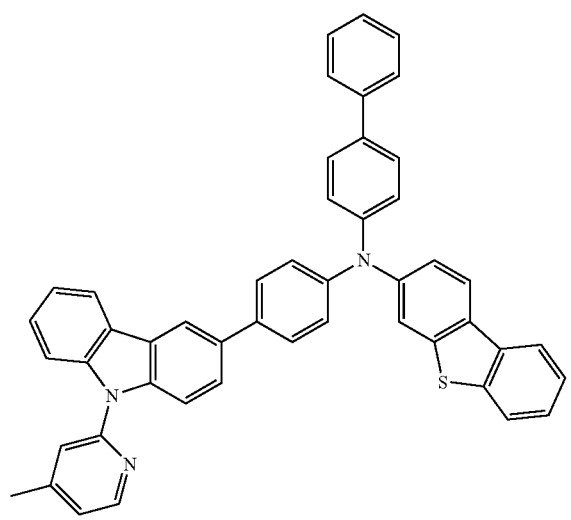
(7)
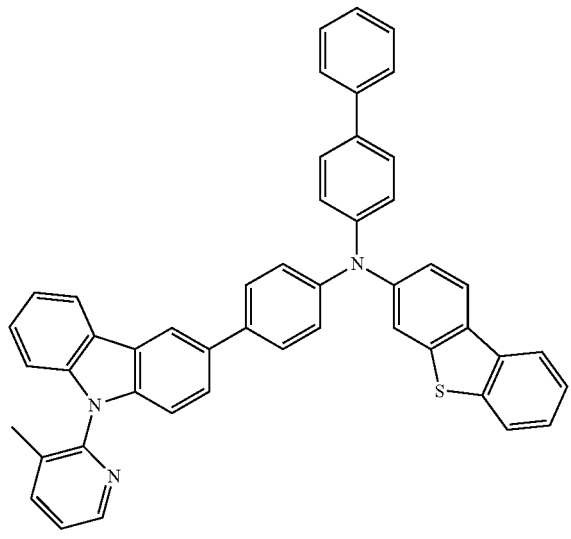
(8)
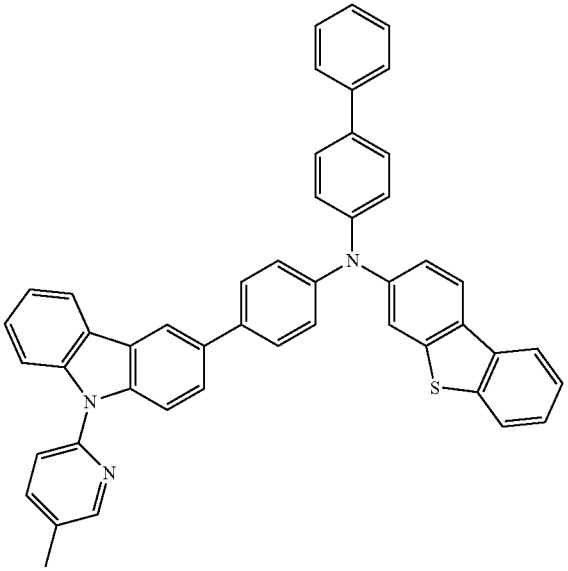
(9)
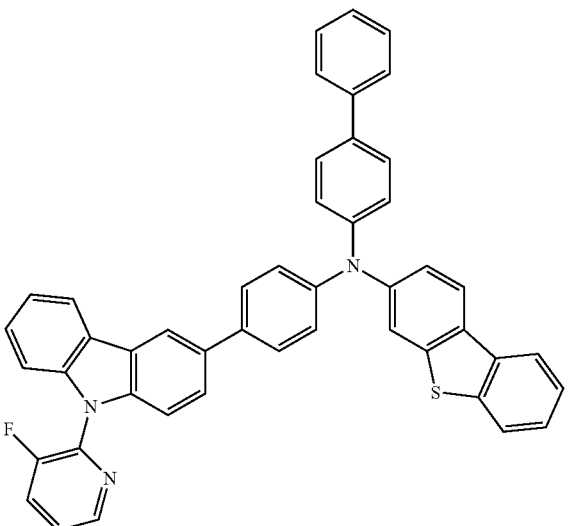
(10)
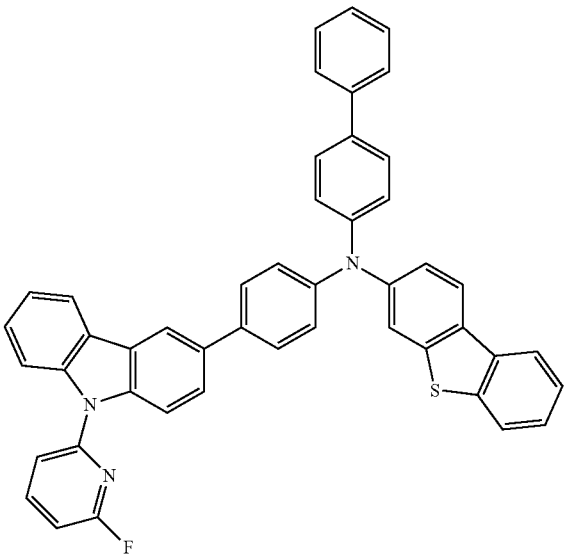

In an implementation, the hole transport material for an organic EL device according to an embodiment may include, e.g., one of compounds 11 to 16, below.
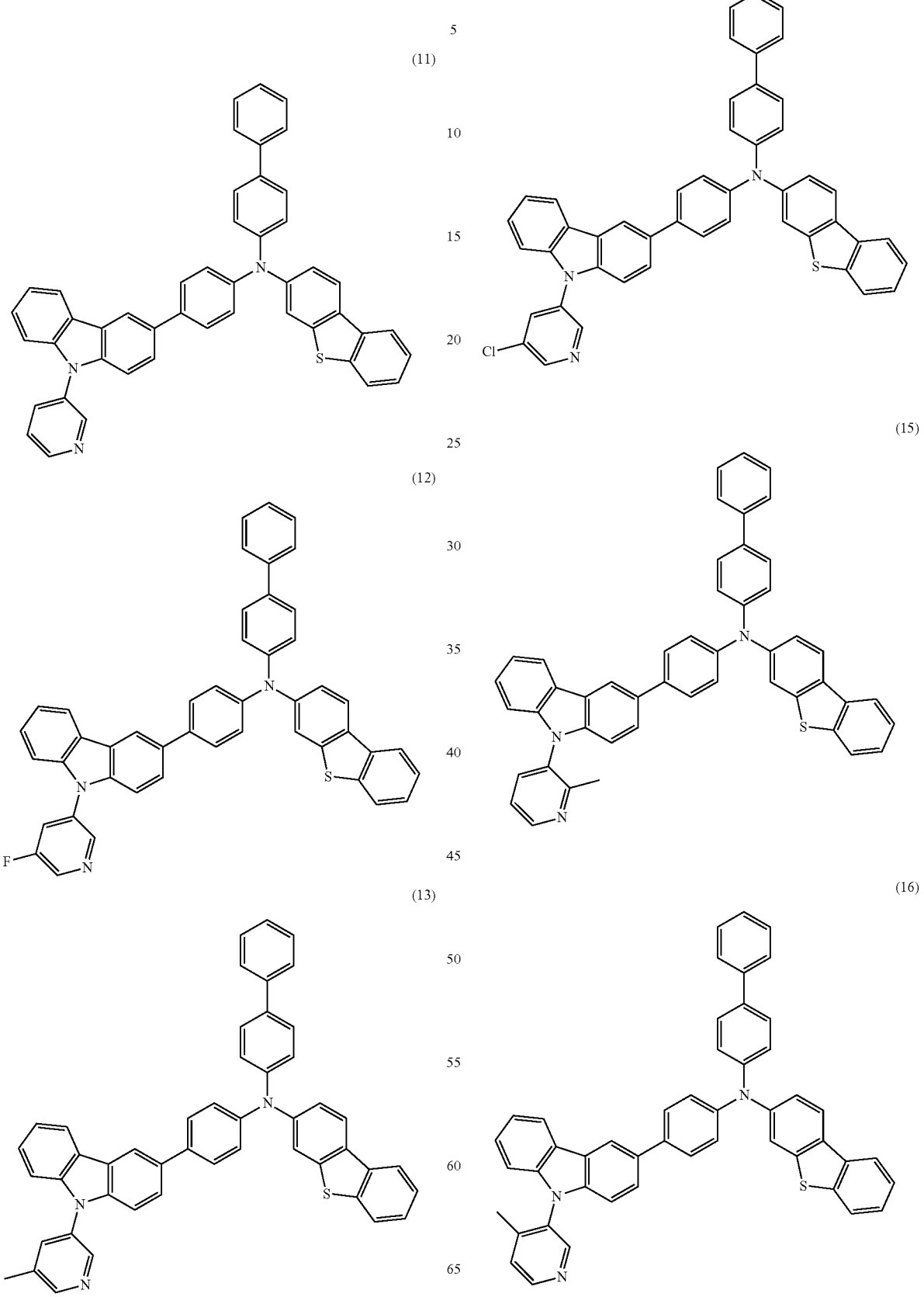

In an implementation, the hole transport material for an organic EL device according to an embodiment may include, e.g., one of compounds 17 to 26, below.
(17)
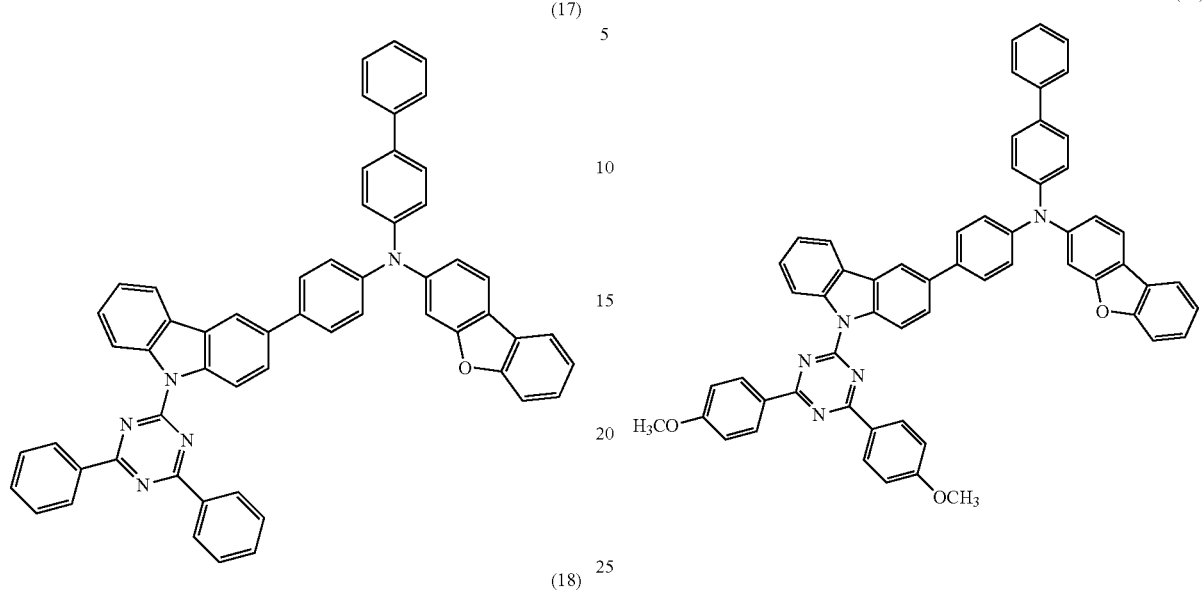
(18)
(20)
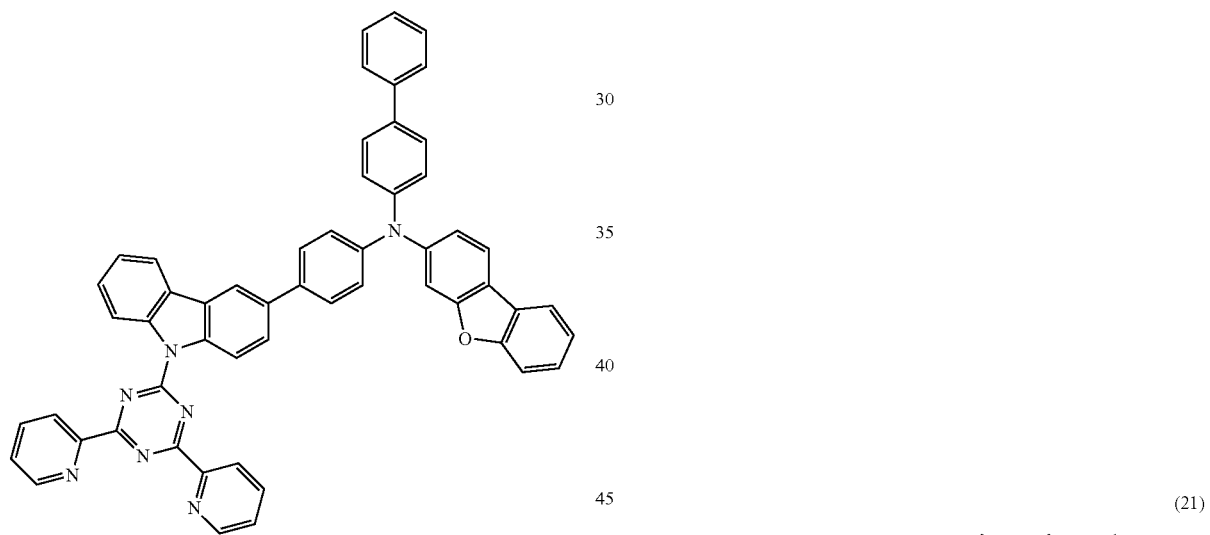
(19)
(21)
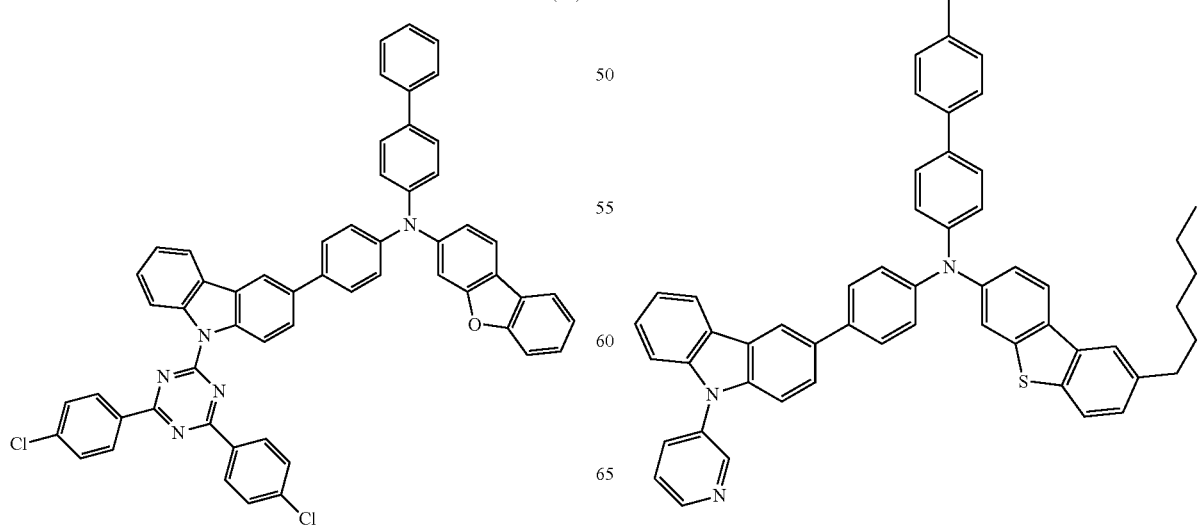

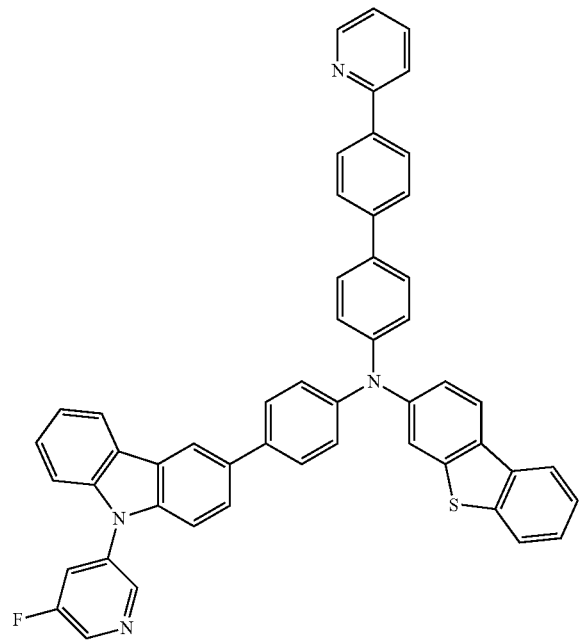
(22)
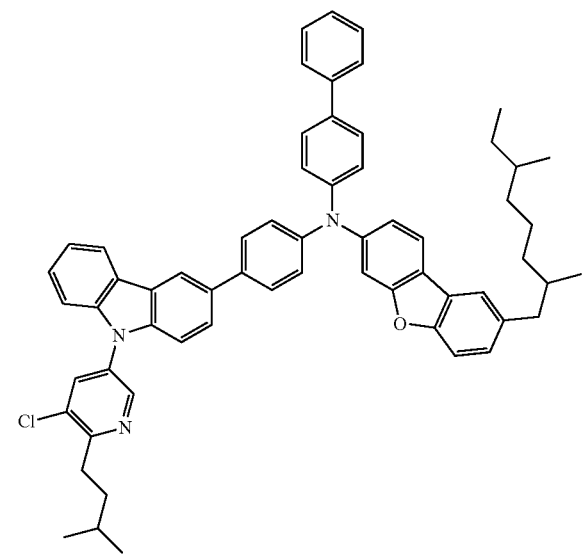
(24)
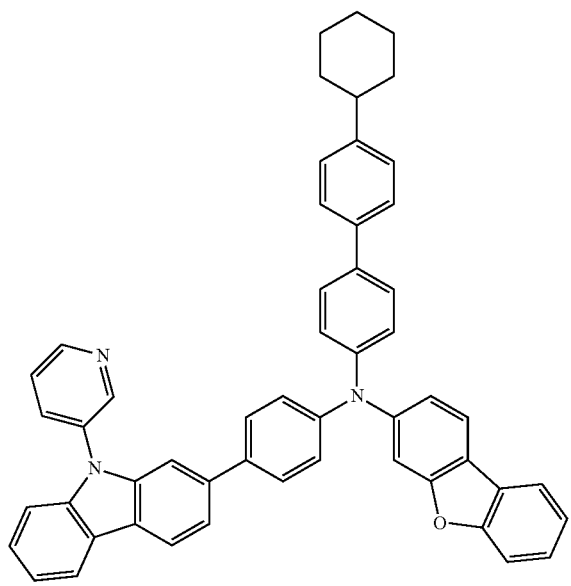
(23)
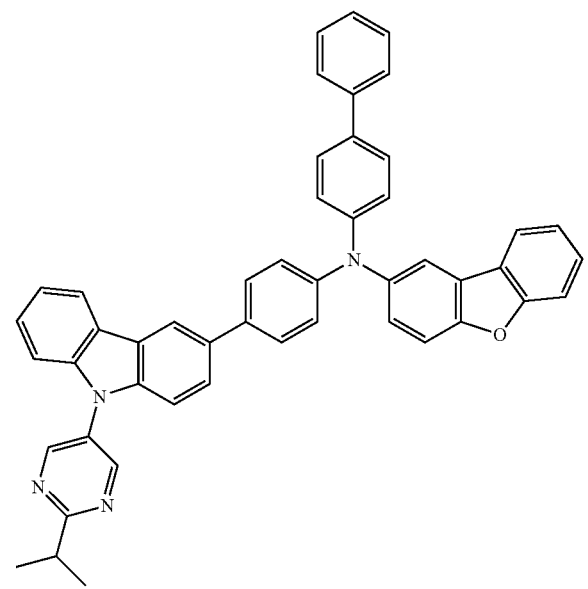
(25)

-continued (26)

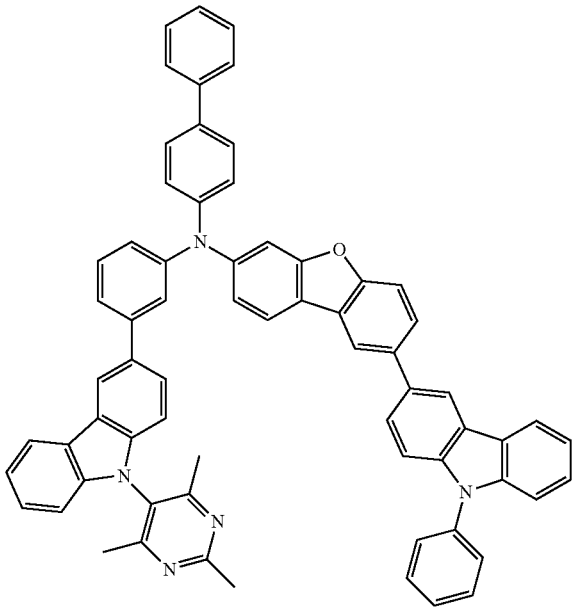

The hole transport materials for an organic EL device according to an embodiment may have the above-described chemical structures, and the hole transport materials may facilitate formation of a high efficiency and long life span hole transport layer for the organic EL device. The hole transport material for an organic EL device according to an embodiment may include a N-(azaaryl)carbazole group in which an azaaryl substituent is included at a position of a nitrogen atom of the carbazole. Also, a hetero ring substituent may be introduced to the carbazole, and resistance to electrons arriving at a hole transport layer (that may not be used in a light-emitting layer) may be improved, and life span may be increased. The hole transport material for an organic EL device according to an embodiment may include, e.g., dibenzofuran or dibenzothiophene, as a hetero ring (e.g., of a fluorene group) substituted on a tertiary amine, and stability may be improved and the life span of the organic EL device may be increased.

Organic EL Device

An organic EL device using a hole transport material according to an embodiment will now be described. FIG. 1 illustrates a schematic cross-sectional view of an organic EL device 100 according to an embodiment. The organic EL device 100 may include, e.g., a substrate 102, an anode 104, a hole injection layer 106, a hole transport layer 108, a light-emitting layer 110, an electron transport layer 112, an electron injection layer 114, and a cathode 116.

The substrate 102 may be, e.g., a transparent glass substrate, a semiconductor substrate formed of silicon or the like, or a flexible substrate formed of a flexible material such as a resin. The anode 104 may be on the substrate 102, and may be formed of, e.g., indium tin oxide (ITO), indium zinc oxide (IZO, or the like. The hole injection layer 106 may be on the anode 104, and may include, e.g., 4,4',4"-tris(N-1-naphtyl-N-phenylamino)triphenylamine (1-TNATA), 4,4-bis(N,N-di(3-tolyl)amino)-3,3-dimethylbiphenyl (HMTPD), or the like. The hole transport layer 108 may be on the hole injection layer 106 and may be formed of a hole transport material for an organic EL device according to an embodiment. The light-emitting layer 110 may be on the hole transport layer 108, and may be formed by doping a host material including 9,10-di(2-naphthyl)anthracene (ADN) with tetra-t-butylperylene (TBP). The electron transport layer 112 may be on the light-emitting layer 110, and may be formed of a material including, e.g., tris(8-hydroxyquinolinato)aluminum (Alq3). The electron injection layer 114 may be on the electron transport layer 112, and may be formed of a material including, e.g., lithium fluoride (LiF). The cathode 116 may be on the electron injection layer 114, and may be formed of a metal such as aluminum (Al), or a transparent material such as ITO, IZO, or the like. The thin layers may be formed by selecting a suitable layer forming method, e.g., a vacuum evaporation, a sputtering, deposition, or the like, according to a material.

In the organic EL device 100 according to the present embodiment, a high efficiency and long life span hole transport layer may be formed by using the above-described hole transport material for an organic EL device. Also, a hole transport material for an organic EL device according to an embodiment may be applied to an active material type organic EL device using TFTs.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

Preparation Method

The above-described hole transport material for an organic EL device was synthesized by a process shown in Reaction Scheme 1.

Reaction Scheme 1

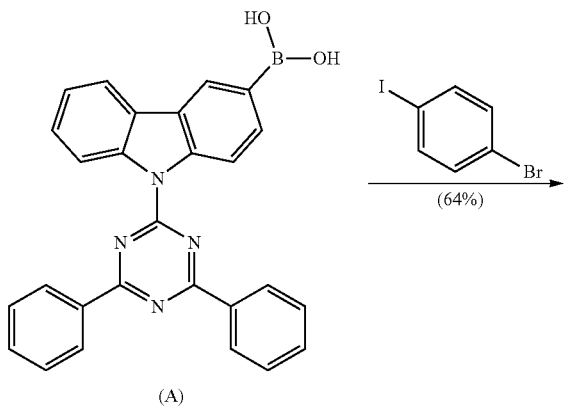

(A)

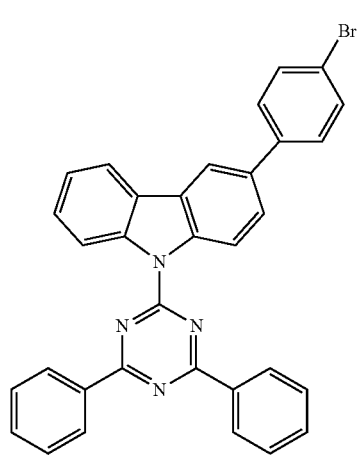

(B)

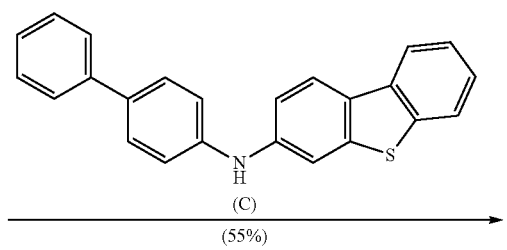

(C) (55%)

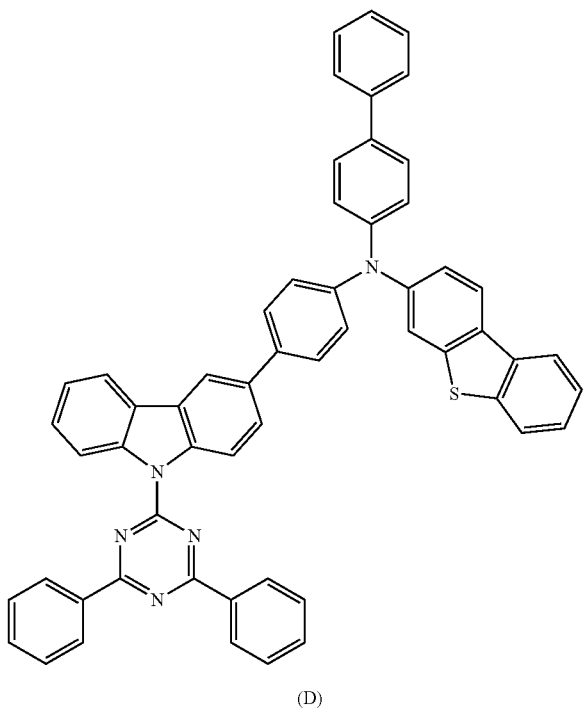

(D)

Synthesis of Bromo type Compound B

Carbazole boronic acid (Compound A) (7.30 g, 16.5 mmol), acetic acid palladium (111 g, 0.495 mmol), tri(o-tolyl)phosphine (302 mg, 0.991 mmol), and 4-bromoiodobenzene (4.91 g, 17.3 mmol) were introduced into a mixture solution of 2 M potassium carbonate aqueous solution (150 mL), toluene (300 mL), and ethanol (150 mL), were heated and refluxed for 8 hours while being stirred under a nitrogen atmosphere. A reaction mixture was extracted using toluene, and an organic layer was sequentially washed using water and a saturated saline solution, and was dried using anhydrous magnesium sulfate. The obtained organic layer was filtered and concentrated, and purified by flash chromatography (cyclohexane/toluene=10/1→3/1) to obtain bromo type compound B (5.85 g, 10.6 mmol, yield: 64%).

Synthesis of Compound D

Bromo type compound B (3.91 g, 7.06 mmol), tris(dibenzylideneacetone)dipalladium(o)-chloroform adduct (219 mg, 0.212 mmol), tri-t-butylphosphine (1.5 M toluene solution, 0.28 mL, 0.42 mmol), and sodium-t-butoxide (1.36 g, 14.1 mmol) were introduced into toluene (200 mL). Dibenzothiopheneamine was added to the mixture solution, and the reaction mixture thus obtained was heated and refluxed for 15 hours while being stirred under a nitrogen atmosphere. A reaction mixture was extracted using toluene, and an organic layer was sequentially washed using water and a saturated saline solution, and was dried using anhydrous magnesium sulfate. The obtained organic layer was filtered and concentrated, and purified by flash chromatography (cyclohexane/toluene=5/1→1/1) to obtain compound D (3.19 g, 3.88 mmol, yield: 55%).

The synthesized compound was identified by measuring a mass spectrum.

The above-described preparation method was used to obtain a compound of Example 1. For comparison, Comparative Example 1 and Comparative Example 2 (2(N,N'-α-dinaphthyl-N,N'-diphenylbenzidine) (α-NPD)) were prepared. Example 1 and Comparative Example 1 are shown below.

Example 1

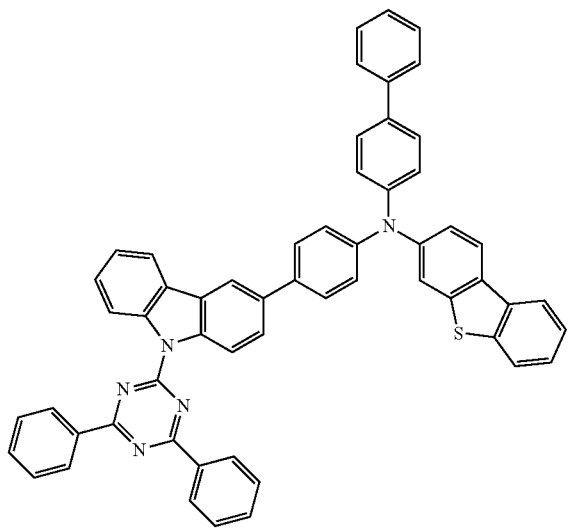

Comparative Example 1

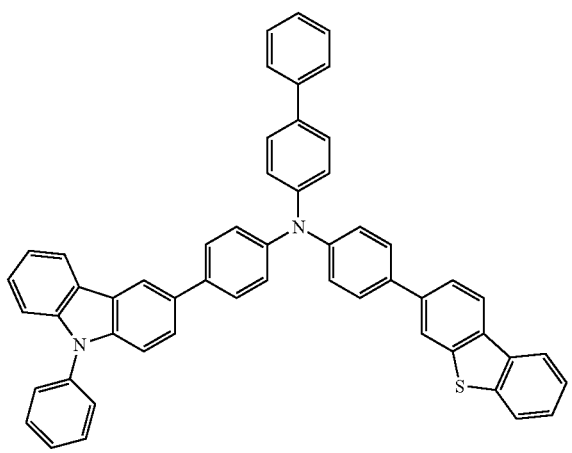

Organic EL devices were manufactured by using Example 1 and Comparative Examples 1 and 2 as hole transport materials. For manufacturing the organic EL devices, a transparent glass substrate was used as a substrate 102, an anode 104 was formed of ITO to a thickness of 150 nm, a hole injection layer 106 was formed of HMTPD to a thickness of 60 nm, a hole transport layer 108 was formed to a thickness of 30 nm, a light-emitting layer 110 in which ADN was doped to 3% with TBP was formed to a thickness of 25 nm, an electron transport layer 112 was formed of Alq3 to a thickness of 25 nm, an electron injection layer 114 was formed of LiF to a thickness of 1 nm, and a cathode 116 was formed of aluminum (Al) to a thickness of 100 nm.

The voltage, current efficiency and half-life of the manufactured organic EL devices were evaluated. Also, the current efficiency indicates a value at 10 mA/cm$^2$, and the half-life indicates a time until the brightness decreased from an initial brightness of 1,000 cd/m$^2$ to half of the initial brightness. The evaluation results are shown in Table 1, below.

TABLE 1

|  | Voltage (V) | Current efficiency (cd/A) | Half life (hour) |
| --- | --- | --- | --- |
| Example 1 | 6.9 | 6.4 | 2,950 |
| Comparative Example 1 | 7.5 | 5.9 | 1,500 |
| Comparative Example 2 | 8.1 | 5.3 | 1,200 |

As may be seen in Table 1, compared to the compounds of Comparative Examples 1 and 2, the compound of Example 1 allowed the organic EL device to be driven at a lower voltage. Also, it may be seen that the compound of Example 1 exhibited a higher current efficiency than the compounds of Comparative Examples 1 and 2. Without being bound by theory, the result may be due to the compound of Example 1 having N-(azaaryl)carbazole at which an azaaryl substituent was introduced as a hetero ring group at a position of a nitrogen atom in carbazole. The compound of Example 1 exhibited a considerably longer half-life than the compounds of Comparative Examples 1 and 2. Without being bound by theory, the result may be due to the facts that the compound of Example 1 (in which an azaaryl substituent was introduced at a position of a nitrogen atom substituted with a tertiary amine) improved the electron affinity and at the same time increased the resistance to electrons.

The hole transport materials for organic EL devices according to embodiments may include an N-(azaaryl)carbazole structure in a molecular skeleton having a tertiary amine and dibenzofuran or dibenzothiophene. Thus, the electron affinity may be improved, the thermal stability may be obtained, and the low voltage operation and long life span of the organic EL devices may be realized.

By way of summation and review, in application of the organic EL device to a display apparatus, high efficiency and long life of the organic EL device are desirable. For realizing the high efficiency and long life, normalization, stabilization, and durability of the hole transport layer may be considered.

Various compounds (e.g., an anthracene derivative, an aromatic amine-based compound, or the like) may be used for a hole transport layer. For example, a carbazole derivative may be advantageous for long life span of an organic EL device. However, in order to promote high efficiency and long life span of an organic EL device, a new hole transport material may be desirable.

The embodiments may provide a hole transport material for a high efficiency and long life span organic electroluminescence device.

The embodiments may provide hole transport materials for providing high efficiency and long life span organic EL devices.

A hole transport material for an organic EL device according to an embodiment may include a N-(Azaaryl)carbazole, the hole transport material may have a high electron affinity and may facilitate driving of the organic EL device at a low voltage.

In the hole transport material for the organic EL device according to an embodiment, a bond between nitrogen atoms may not be formed in ring A, and the hole transport material may be structurally stable and may facilitate obtaining an organic EL device having long life span.

The hole transport material for the organic EL device according to an embodiment may be substituted with a reactive group, and the hole transport material may form a high efficiency and long life span hole transport layer.

The organic EL device according to an embodiment may have a hole transport layer that is formed of a hole transport material into which N-(Azaaryl)carbazole is introduced, and the organic EL device may have a high electron affinity and may be driven at a low voltage In the organic EL device according to an embodiment, a bond between nitrogen atoms may not be formed in ring A, and the organic EL device may be structurally stable and may have a long life span.

The organic EL device according to an embodiment may be formed with a high efficiency and long life span hole transport layer by substituting the hole transport material for the organic EL device with a functional group.

According to an embodiment, a hole transport material for a high efficiency and long life span organic electroluminescence device, and an organic electroluminescence device using the same may be provided.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A hole transport material for an organic electroluminescence device, wherein the hole transport material is one of following compounds (3), (4), (5), (6), (7), (8), (9), (10), (11), (12), (13), (14), (15), (16), (17), (18), (19), (20), (21), (22), (23), (24), (25), and (26):

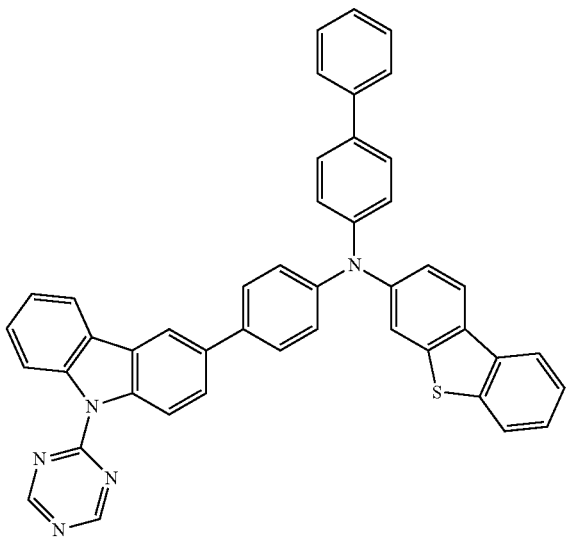

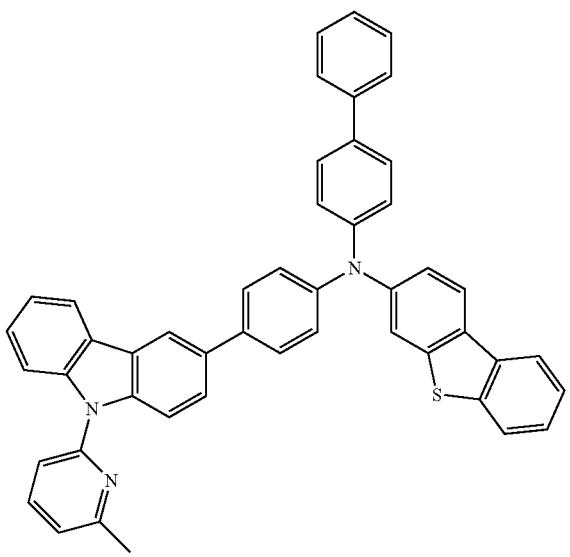

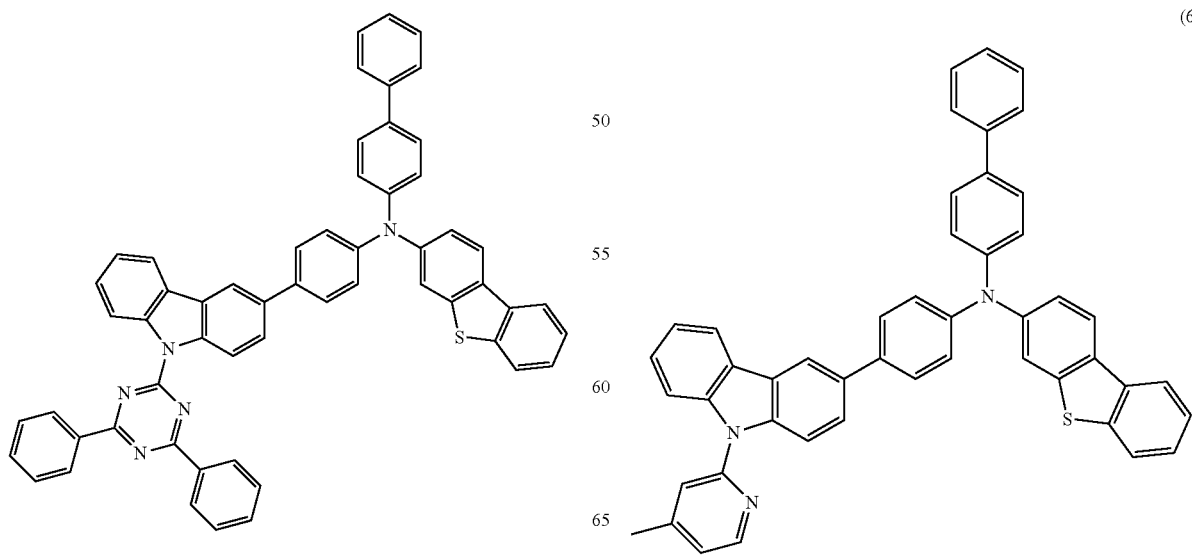

(7)
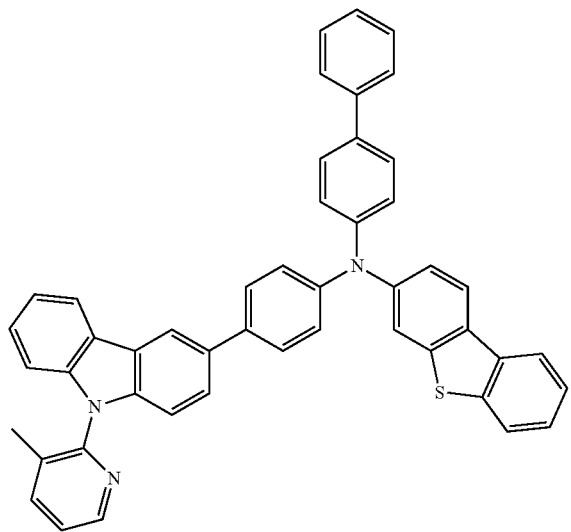
(9)
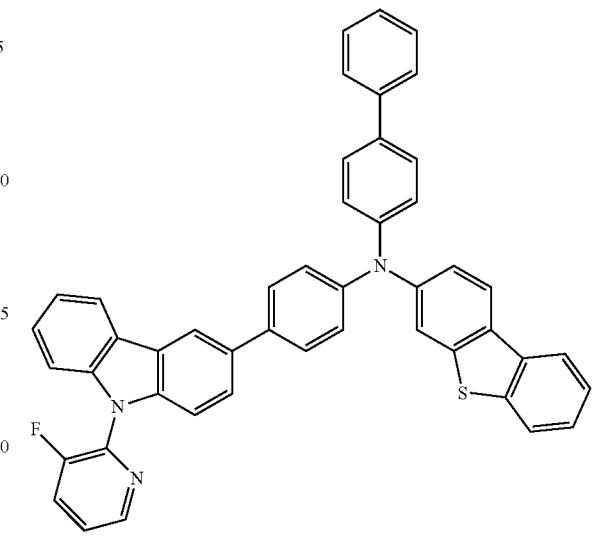
(8)
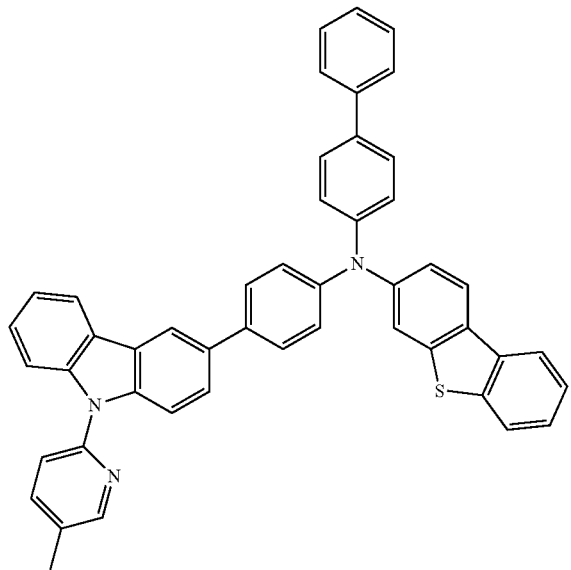
(10)
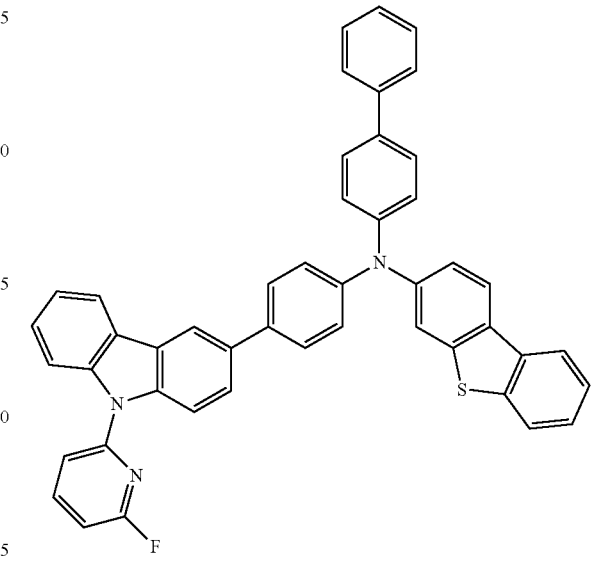

(11)
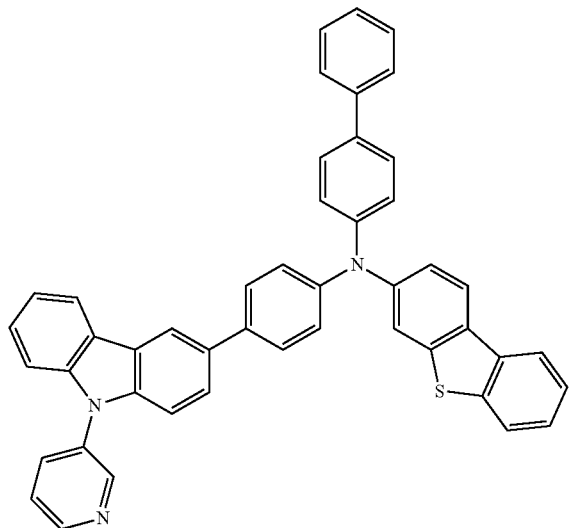
(12)
(13)
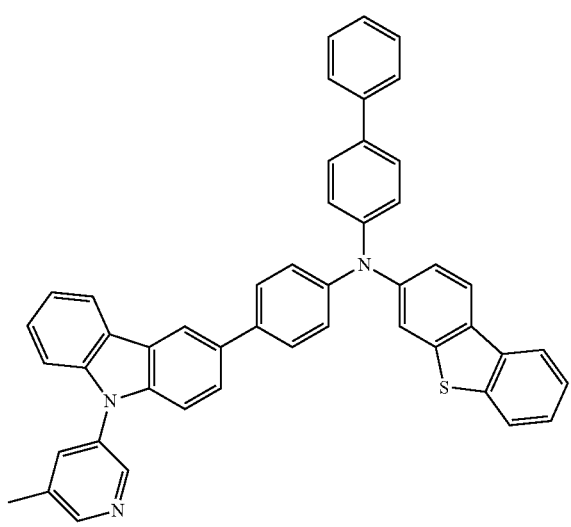
(14)
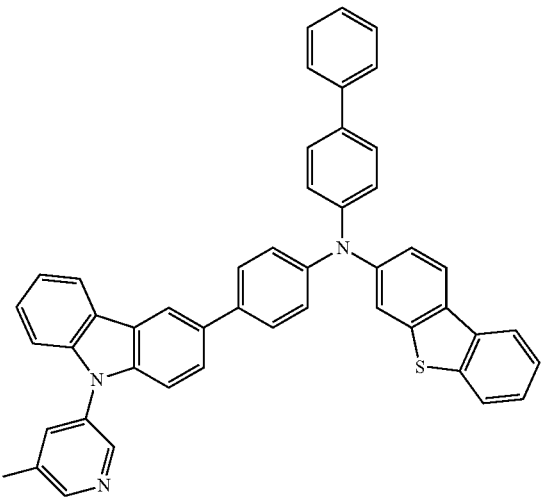
(15)
(16)
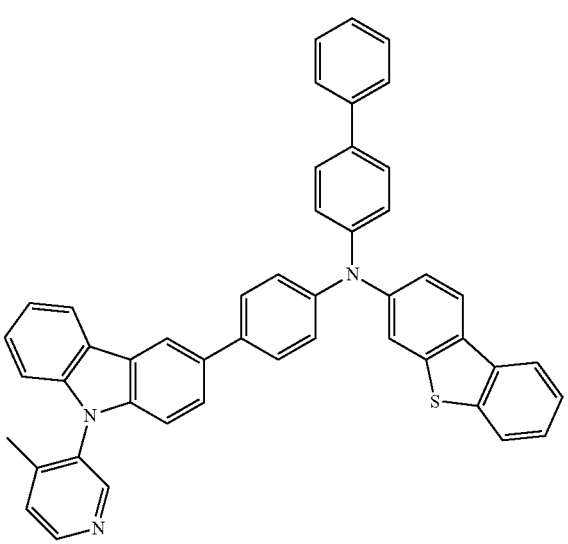

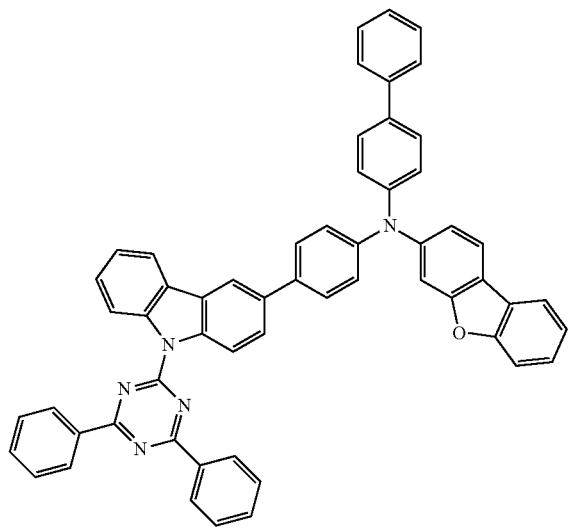
(17)
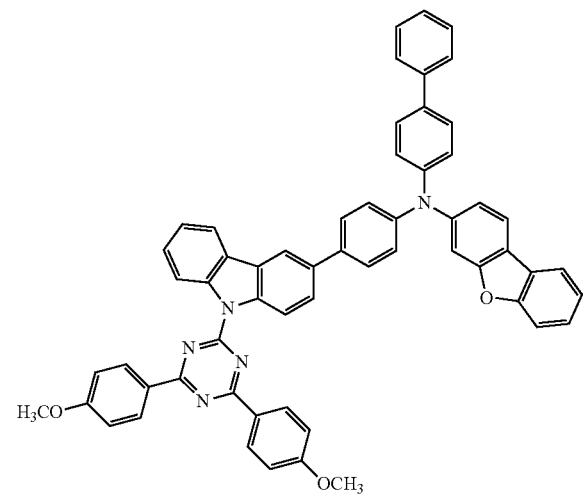
(20)
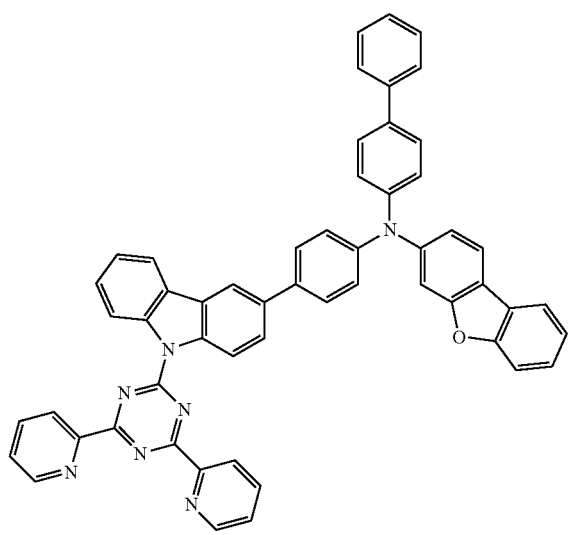
(18)
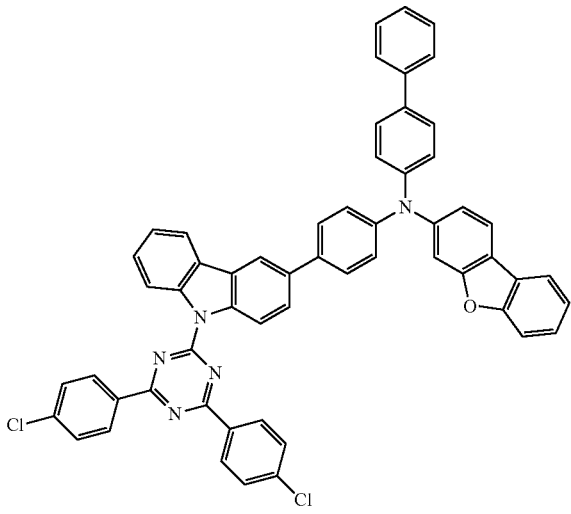
(19)
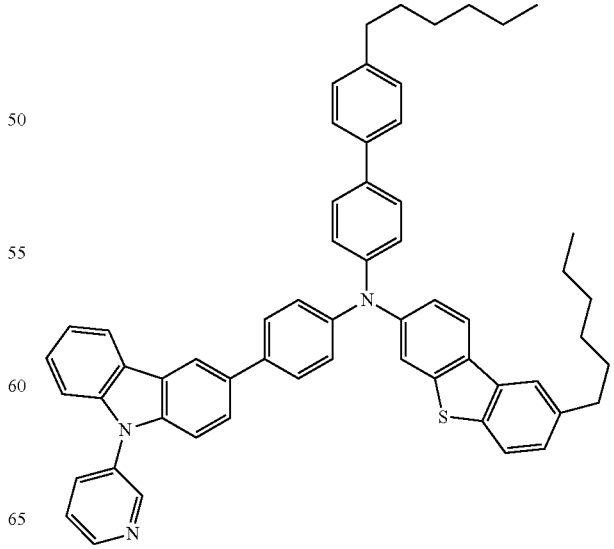
(21)

(22)
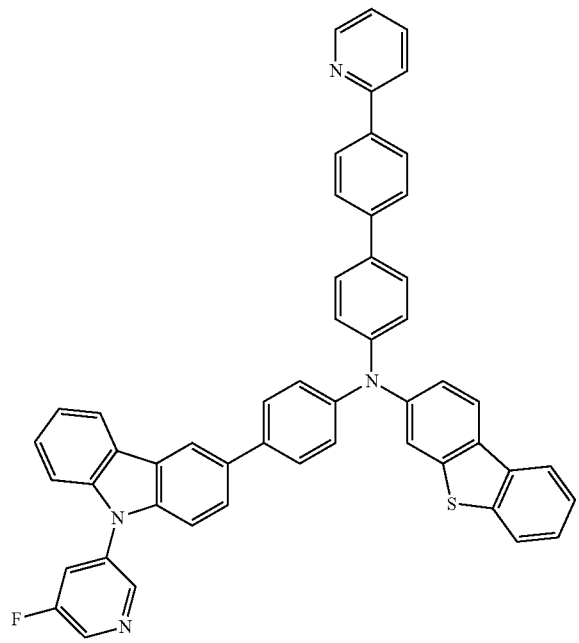
(24)
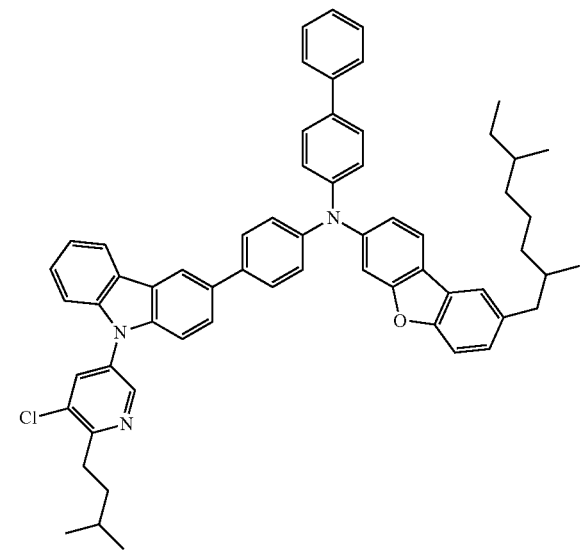
(23)
(25)
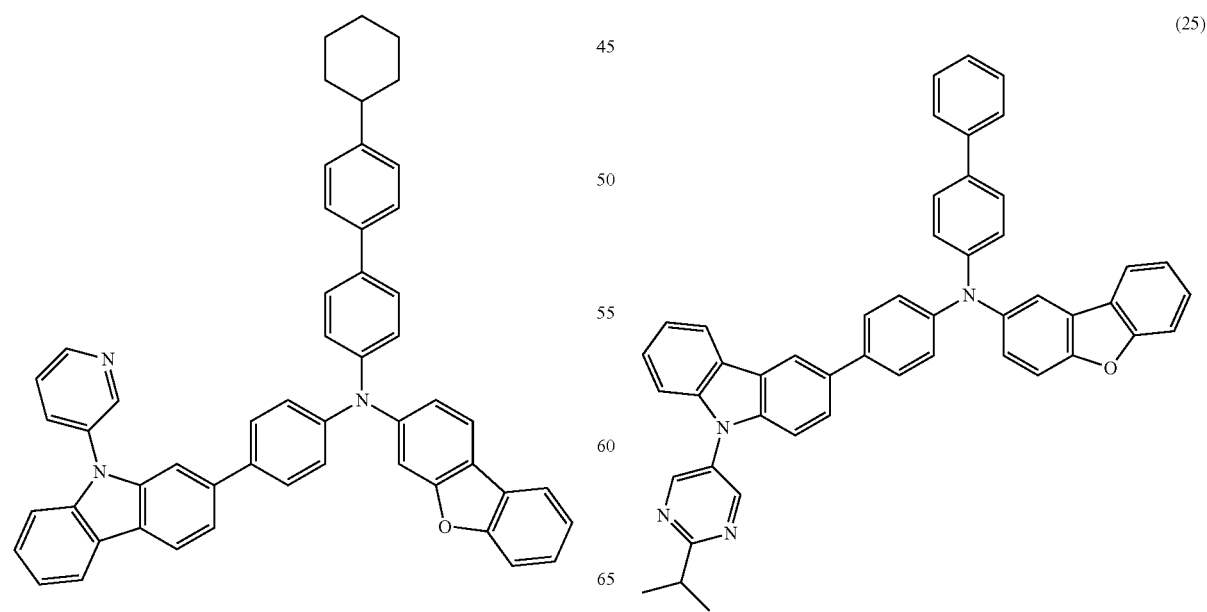

(26)
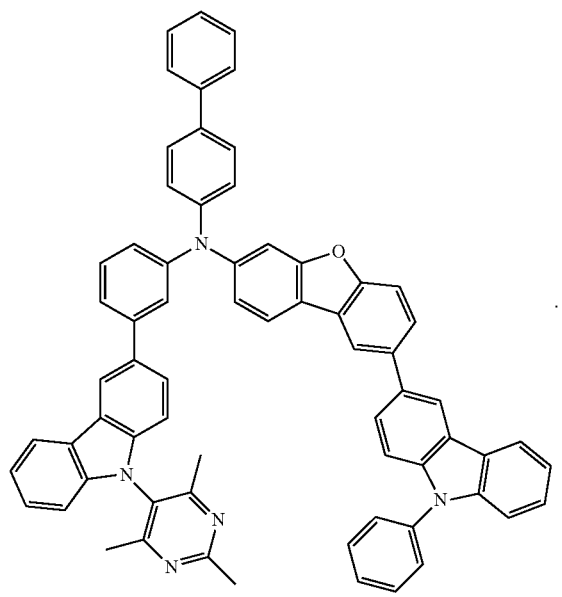
2. An organic electroluminescence device comprising a hole transport material, wherein the hole transport material is one of the following compounds (3), (4), (5), (6), (7), (8), (9), (10), (11), (12), (13), (14), (15), (16), (17), (18), (19), (20), (21), (22), (23), (24), (25), and (26):
(3)
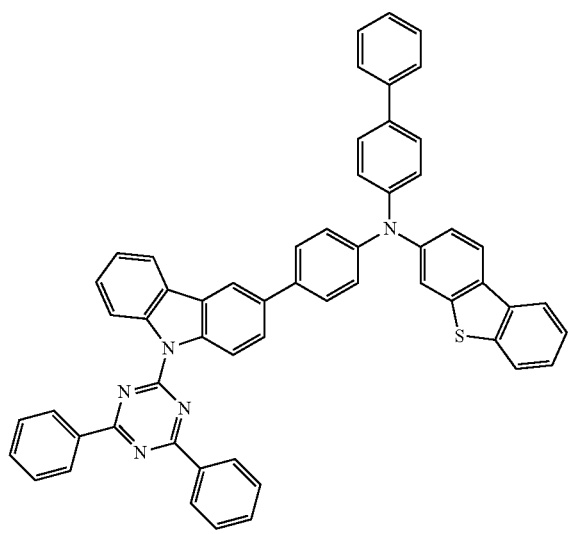
(4)
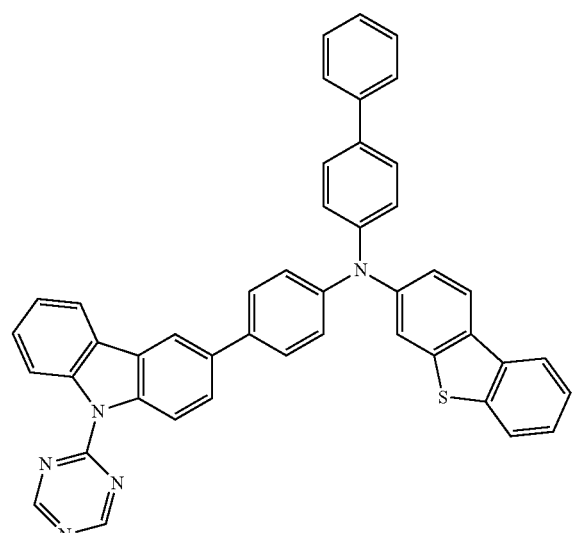
(5)
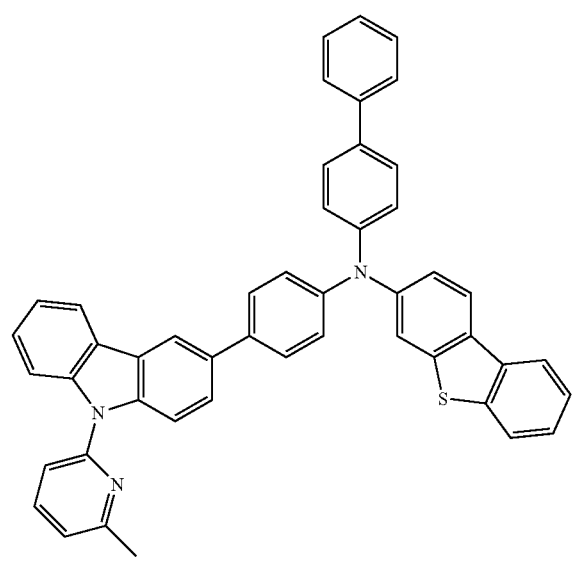
(6)
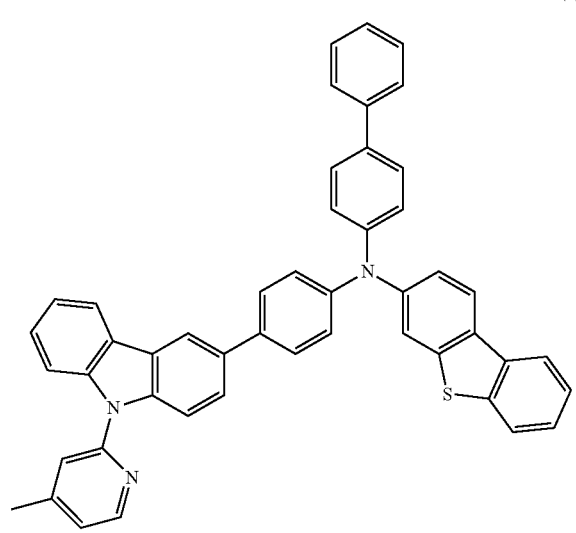

(7)
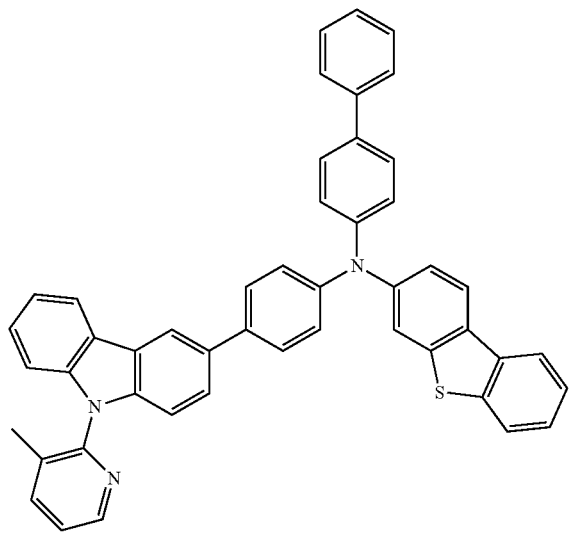
(9)
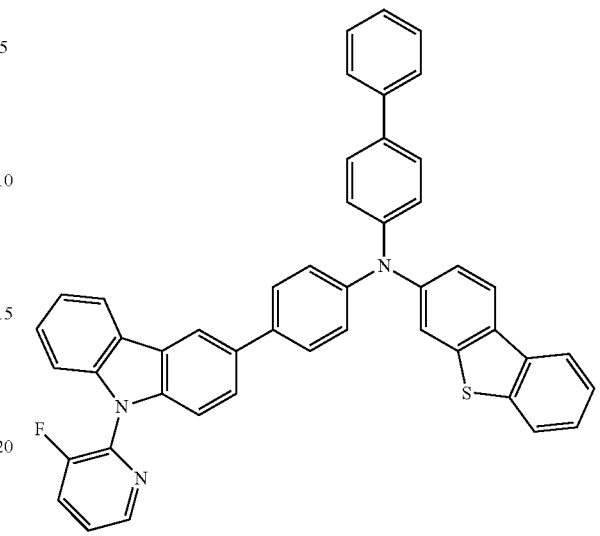
(8)
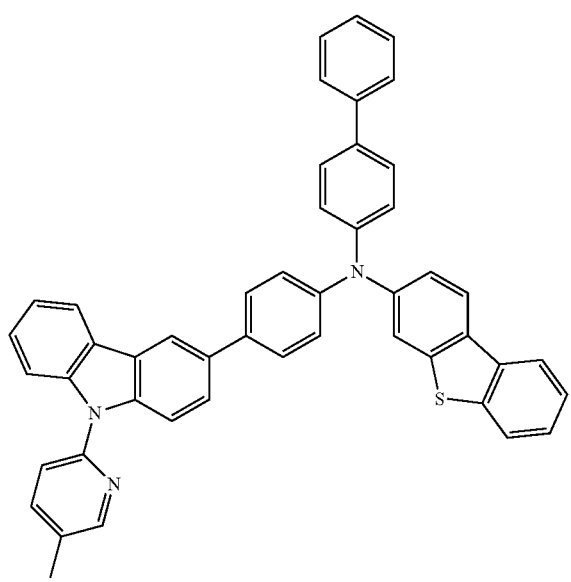
(10)
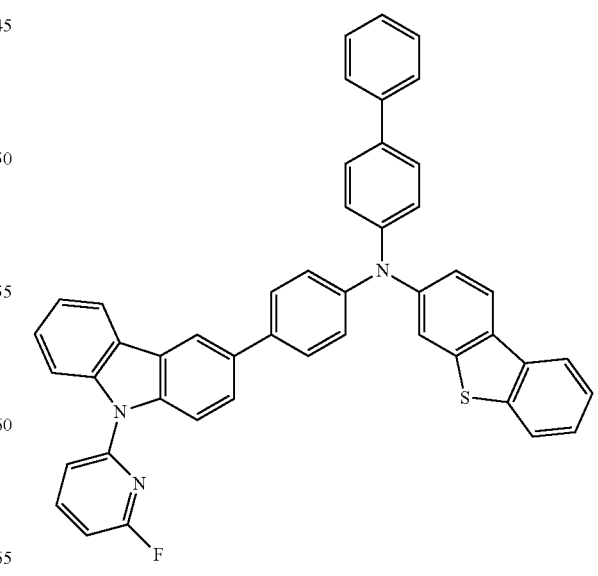

33
-continued
(11)
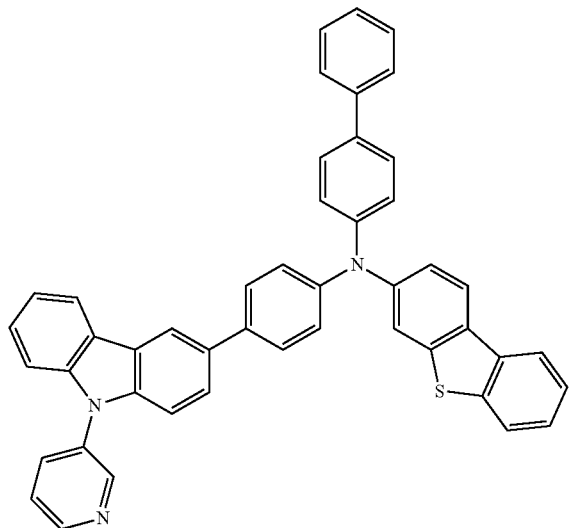
(12)
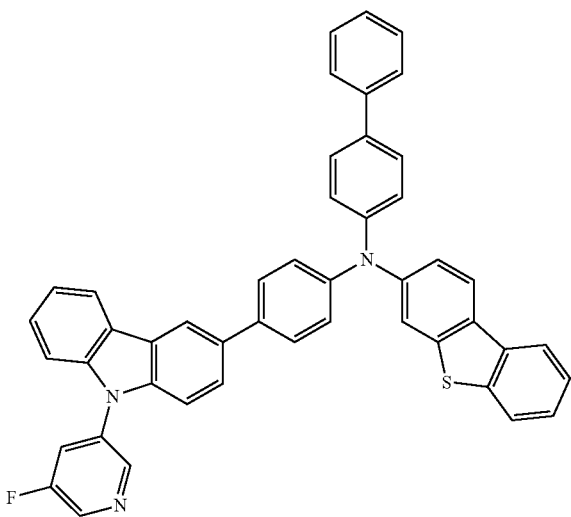
(13)
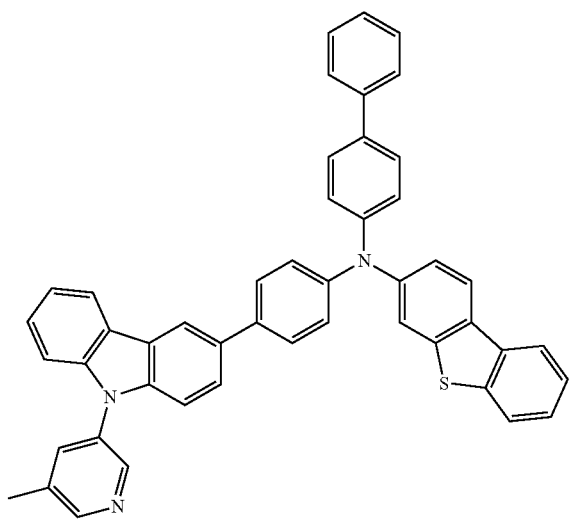
34
-continued
(14)
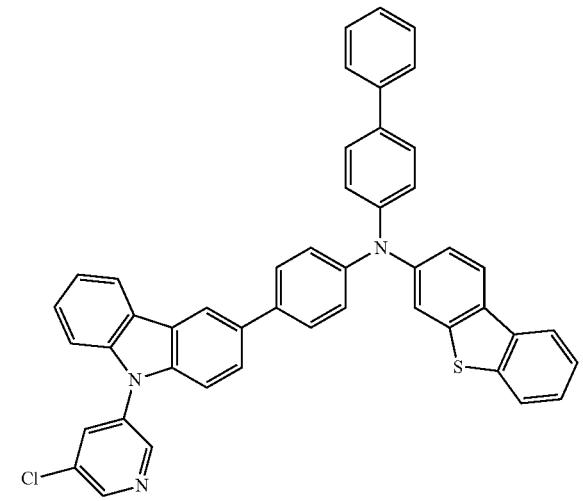
(15)
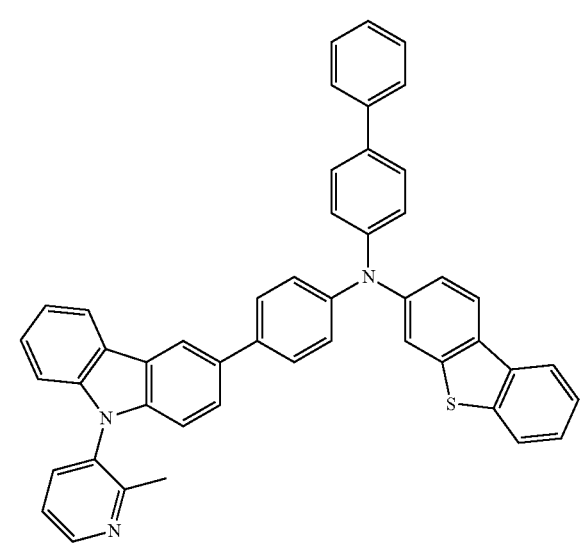
(16)
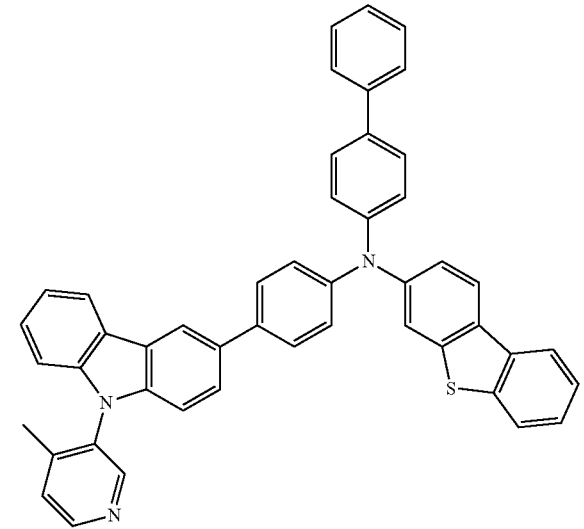

(17)
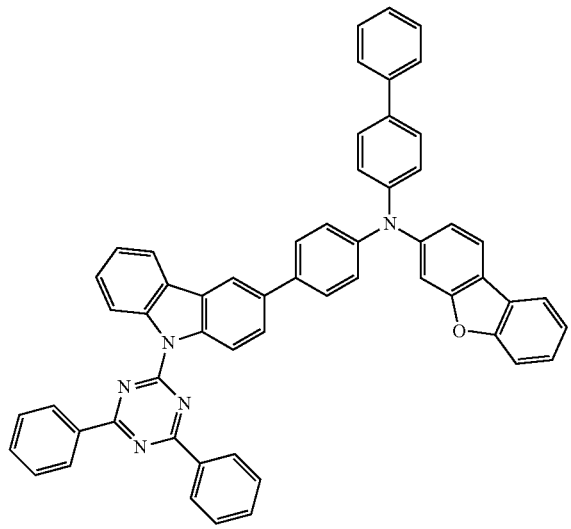
(20)
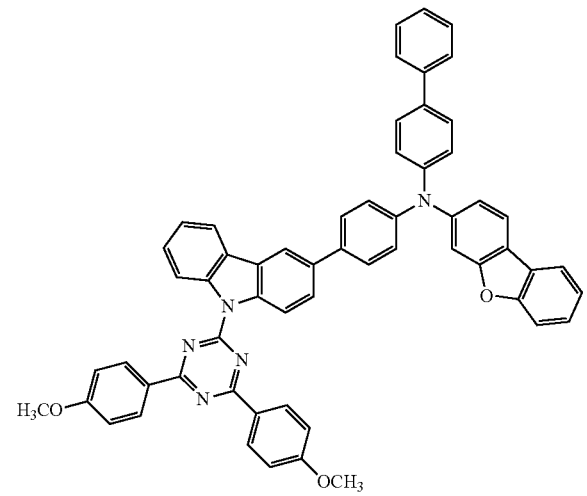
(18)
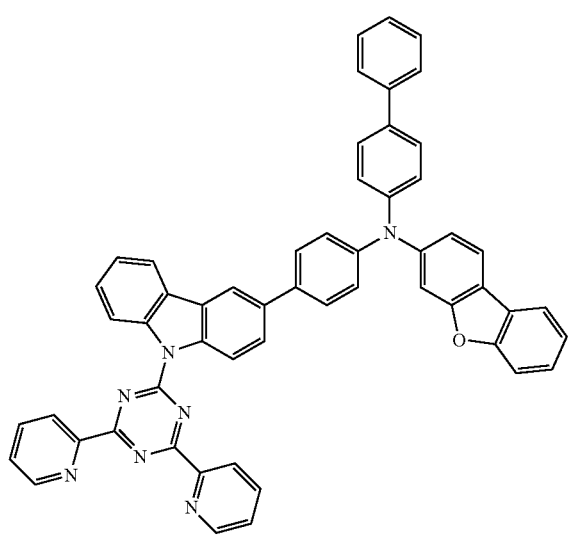
(19)
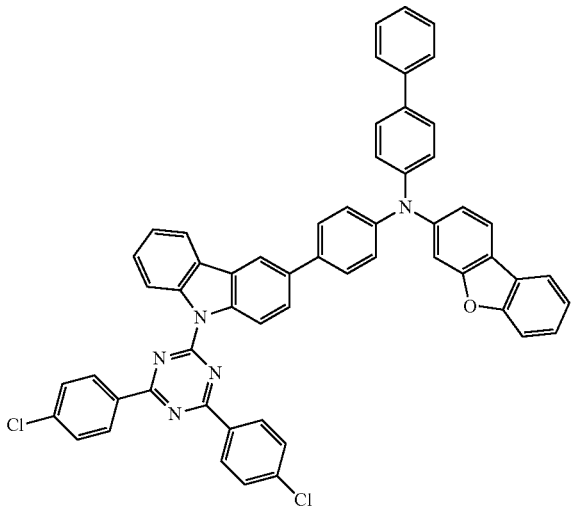
(21)
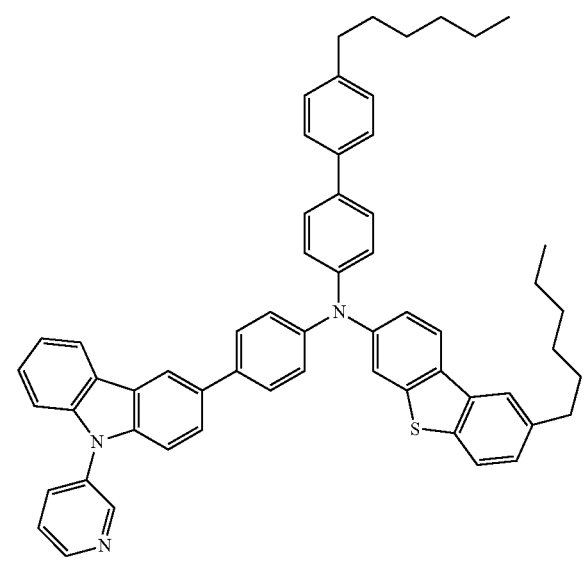

(22)

(23)

(24)

(25)

(26)
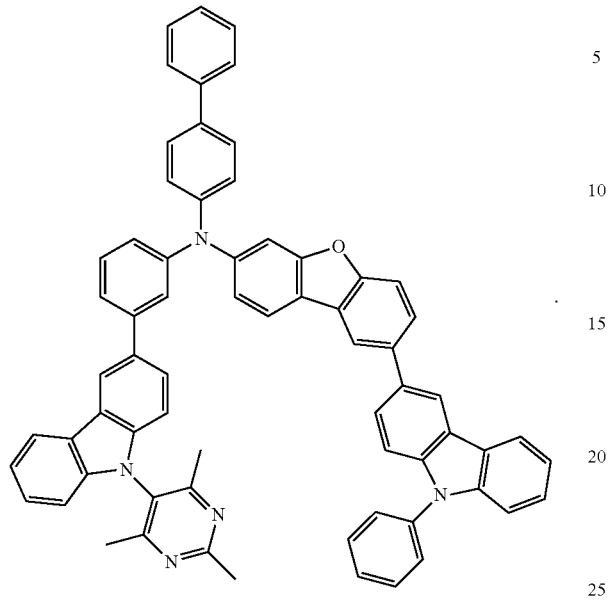
* * * * *